United States Patent [19]

Jungman

[11] 4,090,925

[45] May 23, 1978

[54] PH MEASURING INSTRUMENT AND METHOD

[75] Inventor: Maury Jungman, Bayville, N.Y.

[73] Assignee: J & M Instruments Corp., Bayville, N.Y.

[21] Appl. No.: 712,666

[22] Filed: Aug. 9, 1976

[51] Int. Cl.² ........................................... G01N 27/38
[52] U.S. Cl. .............................. 204/1 T; 204/195 R; 324/30 R; 134/6; 51/296; 51/298 R
[58] Field of Search .............. 204/1 H, 195 R, 196 G; 324/29, 30 R, 30 B; 134/6

[56] References Cited

U.S. PATENT DOCUMENTS

| | | | |
|---|---|---|---|
| 1,668,434 | 5/1928 | Todd | 204/195 R |
| 2,288,180 | 6/1942 | Brengman et al. | 324/30 R |
| 2,311,976 | 2/1943 | Coleman | 204/195 G |
| 2,958,593 | 11/1960 | Hoover et al. | 51/296 |
| 3,073,772 | 1/1963 | Wirz et al. | 204/195 R |
| 3,155,603 | 11/1964 | Hart | 204/195 R |
| 3,161,823 | 12/1964 | Uithoven | 324/29 |
| 3,402,116 | 9/1968 | Kaltenhauser et al. | 204/195 R |
| 3,533,925 | 10/1970 | Inoue | 134/6 |
| 3,574,079 | 4/1971 | Kalman | 204/195 R |
| 4,021,199 | 5/1977 | Mukae et al. | 204/195 R |

OTHER PUBLICATIONS

Orion Instructional Manual Lead Electrode Model, 94-82, 1969, pp. 1-24.

*Primary Examiner*—T. Tung
*Attorney, Agent, or Firm*—Natter & Natter

[57] ABSTRACT

A pH measuring instrument includes a specimen probe having parallel front and rear panels with a planar electrode mounted on each and electrically coupled to a meter movement. Each electrode includes a broad flat electrolytically active surface. The probe is so dimensioned that the active electrode surfaces are parallel and spaced apart a distance less than the gripping capacity between the thumb and forefinger of an operator. A specimen pH value is measured after initial electrode treatment including a dry wiping of the active electrode surfaces, a cleansing of the active electrode surfaces with a plastic filamentous abrasive sponge pad held in one hand and wrapped around both electrodes and an in situ specimen preconditioning. The probe is removed after specimen preconditioning has been attained, recleansed and reinserted in the specimen, after which an accurate pH value measurement is indicated at the meter.

11 Claims, 5 Drawing Figures

PH MEASURING INSTRUMENT AND METHOD

BACKGROUND OF THE INVENTION

1. Field of the Invention

The invention relates to apparatus and techniques for measuring the concentration of an electrolyte in a specimen.

2. Brief Description of the Prior Art

Various devices have been heretofore proposed for determining the pH value or electrolyte concentration of a specimen. A substantial drawback with prior devices has been the difficulties in calibration and inability to maintain consistent reliable readings.

Several pH testing devices were relatively simple in construction and utilized a pair of electrodes of dissimilar materials which were electrically interconnected through a meter. An example of devices of this type is shown in U.S. Pat. No. 3,161,823. Unfortunately, accurate, reliable readings were unobtainable due to various reasons. For example, inaccuracies resulted from temperature factors. Further factors affecting the reliability of such testing devices included contamination of the electrodes which resulted in variations of the readings.

Attempts at providing more accurate and reliable pH testing devices included resort to use of a standard solution of known pH value for calibration during the testing process as exemplified in U.S. Pat. No. 2,604,382. Further devices utilized an intermediate electrolyte between the electrodes and separated from the specimen by a membrane as shown in U.S. Pat. No. 3,413,209. These approaches did not meet with relative success in part due to the complicated procedures involved.

Temperature compensation of pH testing devices has been attempted through the use of compensating resistors as shown in U.S. Pat. No. 3,806,797. Generally, compensated devices were more costly to produce and did not provide a commensurate increase in accuracy or reliability of readings obtained. Further calibration procedures could not adequately compensate for the effects of gradual electrode contamination.

One approach to electrode contamination was disclosed in U.S. Pat. No. 2,454,952 and involved a cleansing procedure which included a series of washings in baths of distilled water, detergent and acetic acid, distilled water again, hydrogen peroxide solution, and the final rinsing with distilled water. Consequently, the use of such device was limited to technicians having adequate reagent supplies to perform the requisite cleansing technique, and the device was unsuitable for use by unskilled persons.

In U.S. Pat. No. 2,288,180 it was suggested that contaminated electrodes could be cleaned by sanding with emery paper, however it has been found after extensive testing that successive emery paper treatments of the same electrode surfaces did not provide an electrolytically active surface of uniform electrode activity. This was possibly due to a multitude of factors; for example, the emery paper itself could have deposited a residue on the electrode and interfered with the electrolytic activity of the electrodes.

SUMMARY OF THE INVENTION

In compendium, the invention comprises a pH measuring instrument having a pair of specimen contacting electrodes, electrically interconnected through a meter. Each electrode includes a flat electrolytically active surface with the surfaces of both electrodes being parallel to one another.

The method of the present invention relates to a technique of using the pH measuring instruments to obtain reliable accurate determinations of the pH value of a specimen. Initially, the electrolytically active surfaces are dry wiped, then cleansed of contaminants with a plastic filamentous abrasive sponge pad supplied with the instrument. Subsequently, the electrodes are deposited in the specimen to provide environmental preconditioning after which the cleansing operation is repeated and the electrodes reinserted to obtain a pH value indication at the meter.

From the foregoing summary, it will be appreciated that it is an object of the present invention to provide a pH measuring instrument of the general character described which is not subject to the disadvantages aforementioned.

A further object of the present invention is to provide a pH measuring instrument which is simple in construction, low in cost, reliable in use, and well adapted for economical mass production fabrication techniques.

Another object of the present invention is to provide a pH measuring instrument of the general character described which lends itself to use by unskilled operators.

Yet another object of the present invention is to provide a pH measuring kit of the general character described which includes a measuring instrument having a pair of electrodes and a plastic filamentous abrasive spongelike pad adapted to be used for the removal of contaminants from the electrodes.

Yet a further object of the present invention is to provide a method of the general character described for determining the pH value of a specimen, which method assures reliable accurate pH determination.

Still a further object of the present invention is to provide a method of the general character described for determining the pH value of a specimen which is simple in operation and does not require the utilization of reagents.

Other objects of the invention in part will be apparent and in part will be pointed out hereinafter.

With these ends in view, the invention finds embodiment in certain combinations of elements, arrangements of parts, and series of steps by which the objects aforementioned and certain other objects are hereinafter attained, all as fully described with reference to the accompanying drawings, and the scope of which is more particularly pointed out and indicated in the appended claims.

BRIEF DESCRIPTION OF THE DRAWINGS

In the accompanying drawings which is shown one of the various possible exemplary embodiments of the invention.

DESCRIPTION OF THE PREFERRED EMBODIMENT

Figure 1:
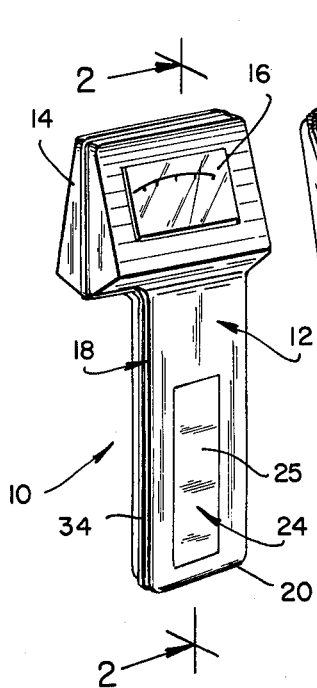
FIG. 1 is a perspective illustration of a pH measuring instrument constructed in accordance with and embodying the invention and showing one of a pair of electrodes secured in a probe which depends from a meter housing.

Referring now in detail to the drawings, the reference numeral 10 denotes generally a pH measuring instrument constructed in accordance with and embodying the invention. The instrument includes an elongate body 12 formed of a moldable material having a relatively high resistivity, e.g. a thermoplastic. The body 12 includes an upper portion comprising a housing 14 for an electrical meter movement 16. In accordance with the invention, the meter movement 16 is adapted to provide an indication of the pH value of a specimen such as a liquid or soil as a function of the measurement of an electromotive force generated between a pair of spaced electrodes implanted in the specimen.

Depending from the upper portion of the meter housing 14 is a probe 18 having a pair of substantially parallel front and rear panels 20, 22 respectively. The probe 18 carries a generally rectangular planar electrode 24, 26 in a mating recess of each panel 20, 22. The depth of each recess approximates the thickness of the respective electrode such that a planar front surface 25, 27 of each electrode 24, 26 is substantially flush with its respective probe panel 20, 22. A layer of cement 28 seals each electrode in its respective panel recess in watertight engagement. The cement 28 may peripherally surround each electrode so that only the front surfaces 25, 27 are exposed and thus serve as the available electrolytically active surfaces. An aperture is provided through the rear wall of each of the panel recesses to facilitate the electrical interconnection between the electrodes 24, 26 and the meter 16. For this purpose, a pair of leads 30, 32 extend from terminals of the meter 16 and are joined, e.g. as by soldering, one to each electrode 24, 26.

It should be appreciated that the body 12 may be formed of a suitable thermoplastic by conventional molding techniques and may be fabricated in two shell halves which are suitably sealed at a longitudinal seam 34. Further, at least in the area of the probe 18 the seam 34 is liquid-tight. Thus, the probe may be inserted into a liquid specimen, e.g. a sample of aquarium water, without leakage into the body 12.

Each electrode 24, 26 is formed of a different metal, e.g. one may be of silver, while the other of magnesium, alternatively one may be of zinc while the other is of aluminum. When the probe 18 is inserted into a specimen such that the electrolytically active surfaces 25, 27 are in full contact with the specimen, the electrolyte concentration of the specimen will provide an electromotive potential between the electrodes, and the meter 16 which includes a movable pointer directly indicates the pH value of the specimen. To determine the pH value of a liquid specimen, mere immersion is sufficient; in a soil specimen the soil is compacted to cover the electrodes.

In accordance with the present invention the electrodes 24, 26 are preconditioned so that repeated accurate pH determinations are obtainable. It is believed that among the major factors contributing to the poor reliability of prior pH measuring instruments was contamination of their electrodes and the difficulty in adequately compensating for temperature induced variations. The present invention provides repeatable, reliable pH determinations by a first thorough cleansing of the electrodes without the use of reagents, an in situ preconditioning of the instrument to the particular specimen, thereafter a withdrawal from the specimen, recleansing to remove contaminants from the electrodes and a final insertion of the probe into the specimen to obtain the pH value indication.

Figure 3:
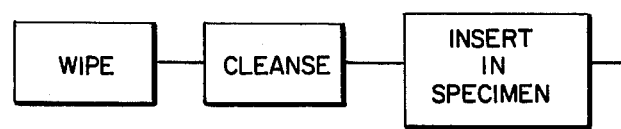
FIG. 3 is a schematized diagram illustrating the various steps for obtaining a pH value determination in accordance with the invention.
Figure 3:
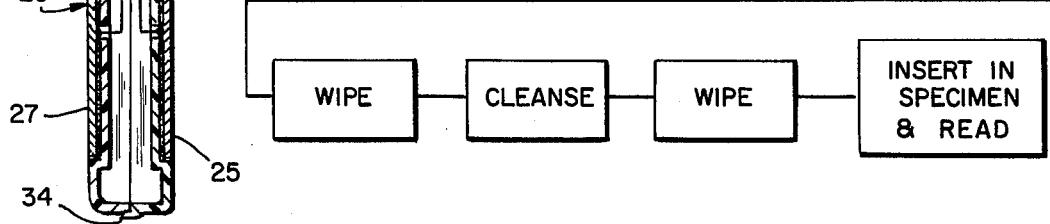

With reference now to FIG. 3 wherein the various stages of the method are depicted, before pH testing, the electrodes are both wiped with an absorbent material, relatively soft and free of oils, grease, or other contaminants. It has been found that a dry unused paper towel has been quite suitable for this purpose. While the wiping procedure may be carried out in any manner, if the piece of paper towel is wrapped to cover both electrolytically active surfaces 25, 27, gripped by the user's hand between the thumb and forefinger and manipulated in a reciprocating motion across the surfaces 25, 27, satisfactory results are expeditiously achieved.

After the wiping procedure has been completed to the extent that no visible particulate material remains on the electrolytically active surfaces 25, 27, the electrolytically active surfaces are cleansed of contaminants by rubbing with a plastic filamentous abrasive pad 36. The pad 36, preferably supplied with the instrument in a kit form, is formed of a fibrous open matrix of linked thermoplastic (e.g. polyamid) filaments. A suitable pad 36 for implementation in the method of the present invention is the nylon based filamentous cleansing pad available from the 3M Company of St. Paul, Minn. under the mark Scotch Brite and designated T Grade Fine. This pad as specified by the manufacturer comprises a nonwoven nylon (polyamid) web and superfine grade flint fines held together by a polymeric resin, e.g. phenolaldehyde; see U.S. Pat. No. 2,958,593.

It should be appreciated that the cleansing pad 36 includes numerous abrasive surfaces dispersed throughout and having an ability to readily adhere abraded particles in the manner analogous to absorption by a sponge. Further, the pad is readily recleanable to remove built up contaminants. It has been found that best results are obtained when using a pad 36 having the ability to absorb abraded particles.

Prior attempts at using various grades of metallic wools, e.g. steel wool, to cleanse the electrodes did not provide uniform consistent pH value determinations, in part possibly due to the residue of cutting oils used in fabricating the wool and further in part possibly due to the inability of the wool to retain contaminants which have been abraded from the electrolytically active surfaces.

Figure 4:
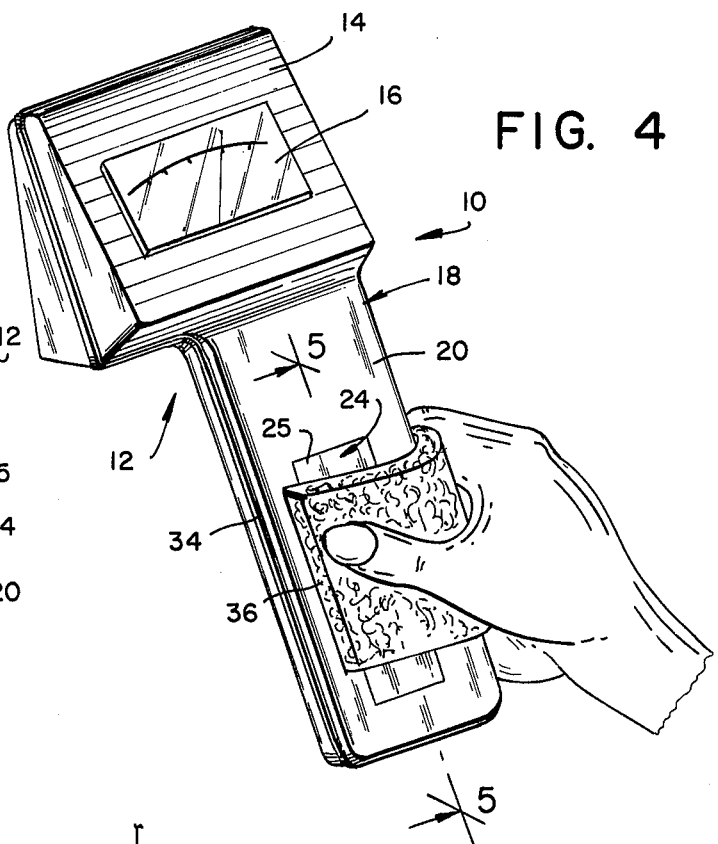
FIG. 4 is a perspective illustration of the procedure for removing contaminants from the electrolytically active surfaces of the electrodes with the employment of a plastic filamentous pad.
Figure 2:
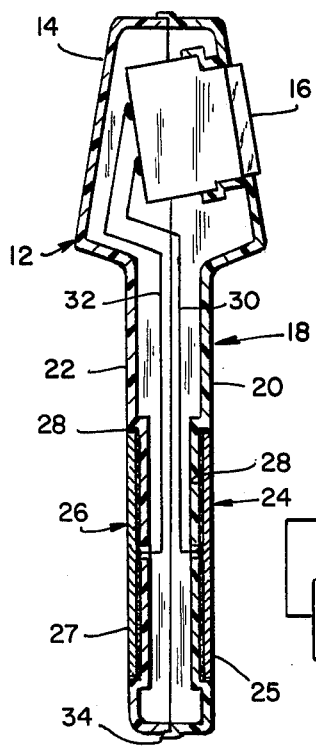
FIG. 2 is a sectional view through the instrument, the same being taken substantially along the plane 2—2 of FIG. 1 and through both electrodes secured in opposite panels of the probe and electrically interconnected to a meter movement.
Figure 5:
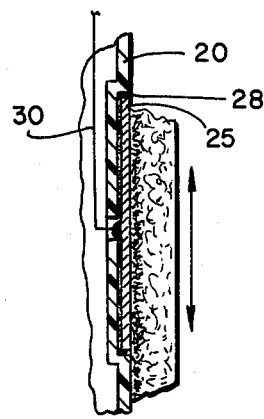
FIG. 5 is a sectional view through one of the electrodes and the pad during the cleansing step, the same being taken substantially along the plane 5—5 of FIG. 4 and illustrating the absorption of electrode contaminants by the pad.

The pad 36 is preferably used to simultaneously cleanse both electrolytically active surfaces by initially being wrapped to cover both surfaces and then gripped between the operator's thumb and forefinger to provide intimate compressive contact between the pad 36 and both active surfaces 25, 27, as shown in FIG. 4. In FIG. 5 it will be seen that with the pad 36 being manipulated in the up and down directions of the heavy arrow, the particulate contaminants which are abraded from the electrolytically active surface 25 are dispersed into the interior fibrous structure of the pad 36 and thus the possibility of a residue contaminant remaining on the active surfaces is eliminated. Satisfactory results have been obtained with the pad 36 being manipulated with between 5 to 7 back and forth strokes across both electrolytically active surfaces 25, 27 with a light to moderate pressure, e.g. one pound compressive force.

After cleansing with the pad 36, the probe 18 is inserted into a specimen so that the specimen completely covers both electrolytically active surfaces 25, 27. When measuring the pH value of soil, it is beneficial at times to moisten and compact the soil around the electrodes. The instrument 10 is environmentally preconditioned to accommodate the specific characteristics of the specimen, e.g. electrolytic activity and ambient temperature, by having the active surfaces 25, 27 remain in intimate contact with the specimen for approximately two to three minutes.

After the preconditioning in situ has been completed, the probe is removed and the electrode surfaces are now recleansed to remove any contaminants which may have been deposited as a result of the electrolytic activity during the preconditioning cycle. The electrolytically active surfaces 25, 27 are therefore rewiped with unused paper toweling in a manner identical to the wiping procedure prior to preconditioning; thereafter both electrolytically active surfaces are cleansed with the pad 36 in a manner identical to the prior cleansing, then the surfaces 25, 27 are again wiped with toweling and finally reinserted into the specimen.

Reliable pH readings are obtainable within five to ten seconds after the reinsertion of the electrodes into the specimen, however the readings generally do not vary with longer intervals, e.g. one minute. It is believed that such period is necessary to allow initial measurable electrolytic reactions to commence, yet not long enough to permit electrode contaminants possibly produced by the electrolytic reaction at the electrodes from impeding with the measurement of pH value.

The precise reasons for the accuracy and reliability of pH determinations obtained in conjunction with the employment of the method of the present invention are unknown, however it is believed that a combination of various factors collectively contribute to the reliable results obtained. Among such factors are the absorption of contaminants by the pad 36 to provide a consistently pure, electrolytically active surface. Cleansing with prior materials such as steel wool or emery paper introduced self-carried contaminants to the electrolytically active surfaces. Further, such prior cleansing materials did not have the capacity to retain abraded contaminants. Thus, the abraded particulate contaminants removed might have remained on the electrodes.

A further reason for the reliability of pH value determinations under the present method might relate to the preconditioning cycle wherein specimen temperature and electrolytic activity factors are self-compensated. Further, in combination with other factors contributing to the reliable results obtained may be the recleansing of the electrolytically active surfaces after specimen preconditioning. This recleansing step probably results in the removal of surface contaminants which may have been produced by electrolytic reactions at the electrodes during the in situ specimen preconditioning. A final possible factor could be that the pH value determination is read within a specified time range after reinsertion into the specimen. Thus, sufficient time has passed to obtain measurable electrolytic reactions, yet the reactions have not proceeded to the extent that electrode contaminants are formed on the electrolytically active surfaces.

Thus, it will be seen that there is provided a pH measuring instrument and kit for determining the pH value of a specimen as well as a method for determining the pH value of a specimen which are well adapted to meet the conditions of practical use.

As various changes might be made in the invention as above set forth, it is to be understood that all matter herein described or shown in the accompanying drawings is to be interpreted as illustrative and not in a limiting sense.

Having thus described the invention, there is claimed as new and desired to be secured by Letters Patent:

1. A method of determining the pH value of a specimen utilizing a measuring instrument including at least two electrodes and means coupling the electrodes to a meter, said method comprising the steps of:
   (a) removing contaminants from the electrodes by cleansing the electrodes in a dry state with a nonwoven polyamid filamentaceous web containing an abrasive material,
   (b) wiping the electrodes with a clean, dry, absorbent, nonabrasive material,
   (c) implanting the electrodes in the specimen, and thereafter
   (d) measuring the pH value of the specimen by observing the meter indication, whereby reliable determination of pH values may be obtained in the absense of distilled water cleansing.

2. A method of determining the pH value of a specimen in accordance with claim 1 wherein the electrodes are wiped after being cleanses with the nonwoven polyamid filamentaceous web and prior to being implanted in the specimen.

3. A method of determining the pH value of a specimen in accordance with claim 1 wherein the electrodes are wiped prior to being cleansed with the nonwoven polyamid filamentaceous web.

4. A method of determining the pH value of a specimen in accordance with claim 3 further including the step of wiping the electrodes with a dry nonabrasive material after cleansing the electrodes with the nonwoven polyamid filamentaceous web and prior to implanting the electrodes in the specimen.

5. A method of determining the pH value of a specimen in accordance with claim 1 wherein the electrodes are cleansed with the application of a compressive force urging the web toward an electrode and the further application of a reciprocally oscillating transverse force in a direction parallel to the electrode surface to be cleansed.

6. A method of determining the pH value of a specimen in accordance with claim 5 wherein the compressive force is of a magnitude in the order of one pound.

7. A method of determining the pH value of a specimen as set forth in claim 1 wherein each electrode includes a planar electrolytically active surface, the electrolytically active surfaces of the electrodes being spaced apart a distance less than the gripping capacity of an operator, the electrodes being cleansed by first wrapping the web about both electrolytically active surfaces and then exerting a manual compressive force against portions of the web to urge said portions in intimate contact against the electrolytically active surface and moving the pad across both electrolytically active surfaces.

8. A method of determining the pH value of a specimen in accordance with claim 7 wherein the web is moved in a reciprocal oscillating course.

9. A method of determining the pH value of a specimen in accordance with claim 8 wherein a compressive force in the order of one pound is applied to urge the portions of the web against the electrolytically active surfaces.

10. A method of determining the pH value of a specimen in accordance with claim 1 further including, prior to said cleansing, wiping and measuring steps, initially cleansing the electrodes with a nonwoven polyamid filamentaceous web, preconditioning the instrument by implanting the electrodes in the specimen, and removing the electrodes from the specimen.

11. A method of determining the pH value of a specimen in accordance with claim 10 further including the step of wiping the electrodes with a clean dry absorbent nonabrasive material prior to the initial cleansing of the electrodes.

* * * * *